(12) United States Patent
Imhof et al.

(10) Patent No.: US 7,798,377 B2
(45) Date of Patent: Sep. 21, 2010

(54) DEVICE FOR ADMINISTERING A LIQUID PRODUCT

(75) Inventors: Erich Imhof, Utzenstrof (CH); Daniel Peter, Niederwangen (CH)

(73) Assignee: Roche Diagnostics International AG, Steinhausen (CH)

( * ) Notice: Subject to any disclaimer, the term of this patent is extended or adjusted under 35 U.S.C. 154(b) by 642 days.

(21) Appl. No.: 11/314,814

(22) Filed: Dec. 21, 2005

(65) Prior Publication Data

US 2006/0151545 A1 Jul. 13, 2006

Related U.S. Application Data

(63) Continuation of application No. PCT/EP2004/006846, filed on Jun. 24, 2004.

(30) Foreign Application Priority Data

Jul. 3, 2003 (DE) .................. 103 30 094

(51) Int. Cl.
*G01F 11/00* (2006.01)

(52) U.S. Cl. .................. 222/386; 222/390; 604/228; 604/131

(58) Field of Classification Search ............ 222/386, 222/390; 604/228, 131, 192, 110; 411/508–510, 411/913; 24/458, 591.1, 663, 676, DIG. 51; 403/329

See application file for complete search history.

(56) References Cited

U.S. PATENT DOCUMENTS

| | | | | | |
|---|---|---|---|---|---|
| 2,473,733 | A | * | 6/1949 | Smith | .................. 604/192 |
| 2,509,192 | A | * | 5/1950 | Ougljesa | .................. 411/508 |
| 3,115,804 | A | * | 12/1963 | Johnson | .................. 411/338 |
| 3,466,966 | A | * | 9/1969 | Brown | .................. 411/510 |
| 4,144,885 | A | * | 3/1979 | Stait | .................. 604/218 |
| 4,180,069 | A | | 12/1979 | Walters | |
| 4,677,980 | A | * | 7/1987 | Reilly et al. | .................. 600/432 |
| 4,680,838 | A | * | 7/1987 | Astl | .................. 24/442 |
| 4,728,238 | A | * | 3/1988 | Chisholm et al. | .................. 411/510 |
| 4,770,585 | A | * | 9/1988 | Astl | .................. 411/446 |
| 4,911,695 | A | * | 3/1990 | Lindner | .................. 604/228 |
| 6,017,330 | A | * | 1/2000 | Hitchins et al. | .................. 604/218 |
| 6,196,999 | B1 | * | 3/2001 | Goethel et al. | .................. 604/131 |
| 6,485,465 | B2 | * | 11/2002 | Moberg et al. | .................. 604/154 |
| 6,817,990 | B2 | * | 11/2004 | Yap et al. | .................. 604/228 |
| 7,004,702 | B2 | * | 2/2006 | Van Der Heijden | .................. 411/438 |
| 2002/0072720 | A1 | * | 6/2002 | Hague et al. | .................. 604/264 |
| 2004/0073160 | A1 | * | 4/2004 | Pinkerton | .................. 604/28 |

FOREIGN PATENT DOCUMENTS

CA 651985 A * 11/1962

(Continued)

*Primary Examiner*—Kevin P Shaver
*Assistant Examiner*—Robert K Nichols, II
(74) *Attorney, Agent, or Firm*—Dorsey & Whitney LLP (57) ABSTRACT

A device for dispensing a substance, including a receptacle for the product, a piston plug axially moveable in the receptacle, an output member associated with the device for causing the piston plug to move axially, and a connecting mechanism for detachably connecting the output member to the piston plug by axially displacement of the output member and the piston plug relative to each other, wherein, after being connected, the output member and piston plug may be separated by relative twisting.

26 Claims, 5 Drawing Sheets

FOREIGN PATENT DOCUMENTS

| | | |
|---|---|---|
| DE | 27 15 969 | 2/1978 |
| DE | 27 33 526 | 3/1978 |
| DE | 70 24 161 | 10/1979 |
| EP | 0 346 950 A2 | 12/1989 |
| FR | 2020029 * | 7/1970 |

* cited by examiner

DEVICE FOR ADMINISTERING A LIQUID PRODUCT

CROSS REFERENCE TO RELATED APPLICATION(S)

This application is a continuation of International Application No. PCT/EP2004/006846, filed on Jun. 24, 2004, which claims priority to German Patent Application No. DE 103 30 094.5, filed on Jul. 3, 2003, the contents of both applications are incorporated in their entirety herein by reference.

BACKGROUND

The invention relates to devices for dispensing, delivering, administering or injecting substances and to methods for making and using them. More particularly, it relates to a medical device for the administration, including metered administration, of a liquid product or substance that contains a medical or therapeutic agent, more particularly insulin for treating patients with diabetes.

For metered administration, liquids that contain a medical or therapeutic agent are commonly stored in a liquid receptacle in which a piston plug is mounted so that it is axially movable. The piston plug is moved axially toward an outlet of the liquid receptacle by an output member of a drive mechanism, so as to cause liquid to be dispensed from the liquid receptacle. It is preferable in this case that the liquid receptacle is exchangeable. This requires a connecting mechanism for releasably connecting the piston plug to the output member. For exact metering of the liquid that is to be administered, the connecting mechanism must be such that the connection between piston plug and output member is secured against axial displacement of the output member relative to the piston plug, for example in order to prevent the liquid receptacle from self-emptying as a result of what is known as a siphoning effect.

From the prior art, it is known to provide the output member with a bead which engages in an undercut on the rear face of the piston plug. Such a connection can be established and released again only with difficulty. From the prior art, it is also known to provide the piston plug and the front end of the output member with a thread and an opposing thread, respectively, so that a connection can be established by screwing the output member onto the piston plug and this connection can be released again by unscrewing the output member from the piston plug. The ampoule, with the piston plug held in it, is usually screwed onto the output member by hand. This method of connecting may be difficult for some people, for example the elderly, frail or those with joint problems. It is time-consuming, and problematic if the positions of the output member and of the piston plug do not agree or if they are not aligned properly. During screwing, liquid may be inadvertently dispensed or air may be drawn into the liquid receptacle. Intake of air should be avoided in particular, as this can lead to therapy complications.

SUMMARY

An object of the present invention is to provide a device for the administration of a product, including metered administration, with a connecting mechanism for connecting components of the device, e.g., a piston plug and an output member, whereby the connection can be made and released easily.

In one embodiment, the present invention comprises a device for dispensing a substance, comprising a receptacle for the product, a piston plug axially moveable in the receptacle, an output member associated with the device for causing the piston plug to move axially in the receptacle, and a connector for detachably connecting the output member to the piston plug by axially displacing at least one of the output member and the piston plug relative to the other, wherein, after being connected, the output member and piston plug may be separated by relative twisting.

According to one embodiment of the present invention, concerning a device with a connecting mechanism in which the connection between a piston plug and output member can be released again by relative twisting between piston plug and output member, the connecting mechanism is configured such that the connection between the piston plug and output member can be established by axially advancing the output member relative to the piston plug. It is advantageous that the drive mechanics of the injection or infusion device, in which the liquid receptacle is to be fitted, do not have to be specially configured for exchange of the liquid receptacle. Instead, the axial advance movement of the output member, for which the mechanics of injection or infusion devices are typically configured, can also be used to establish the connection between the piston plug and output member. Thus, according to the invention, by advancing the output member and/or by inserting the liquid receptacle, a suitable mechanical connection between piston plug and output member is achieved which is sufficiently stable for exact metering of a dose of liquid to be administered. Examples of such a mechanical connection are a lock, a catch or a snap-fit connection.

During the axial advance of the output member to the piston plug, the output member is preferably not rotated. According to the invention, however, a simultaneous rotation of the output member during the axial advance movement may in principle be permitted for establishing the connection.

To establish the connection, in one embodiment it is preferable for the output member itself, or for a front end of the output member, to be pushed into the piston plug and/or for the piston plug to be pushed over the output member. In such an embodiment, the output member, preferably its front end, is provided with means for establishing the mechanical connection, for example suitable locking, catching or snap-fit means. These means are received in the piston plug by correspondingly configured elements, for example by correspondingly configured locking, catching or snap-fit means which, in particular, can be formed by the threads of conventional piston plugs.

To establish the mechanical connection, the output member can preferably be advanced in a substantially unimpeded manner, without an appreciable drive force being exerted on the piston plug. This should also be true in embodiments wherein the connection is achieved through insertion of the liquid receptacle. It is advantageous if, when establishing the mechanical connection, no unwanted advancing force is exerted on the piston plug, as this would, of course, cause unwanted or unintentional dispensing of liquid. For this purpose, the connecting mechanism is designed such that it is able to yield, so that, during the axial advance of the output member, the elements of the connecting mechanism which bring about the mechanical connection are able to yield and/ or are resilient and/or unlocked as long as the mechanical connection, effected, for example, by locking, catching or snap-fitting, is not yet established. Thus, after the mechanical connection has been established, the elements of the connecting mechanism which bring about the mechanical connection secure the connection against axial displacement of the output member relative to the piston plug.

It is also advantageous that, for example even in the case of an only half-filled liquid receptacle, a connection between piston plug and output member can still be reliably established without the piston plug being axially displaced by an axial force acting on the piston plug as the mechanical connection is being established. With an only partially filled liquid receptacle, there is in fact a danger that, if the output member and piston plug having axial positions that do not match one another, the piston plug will either be pushed forward in the advancing direction and liquid will therefore be dispensed from the liquid receptacle, or the piston plug will be drawn back counter to the advancing direction and, as a result, air may be sucked into the liquid receptacle. In principle, however, this danger also exists in cases where the liquid receptacle is full.

In some preferred embodiments of the present invention, the device is provided with an arrangement by means of which the output member for establishing the connection with the piston plug is moved in the advancing direction, preferably by a motor. In some preferred embodiments, the device also comprises an arrangement which detects when the output member and the piston plug are correctly connected to one another and/or also when the output member is locked together with the piston plug. Such a detection arrangement can comprise a sensor for measuring an axial force or torque acting on the output member. The time at which the output member is correctly positioned in the piston plug is signalled by a change in the axial force or torque measured by the sensor. The change in the measured parameter, for example the axial force or the torque, can derive from the wall friction between the piston plug and the liquid receptacle and/or from the flow resistance in a catheter joined to the outlet of the liquid receptacle. Evaluation of the flow resistance does, of course, involve an attached catheter or the like. However, this is not a disadvantage, since the catheter has to be filled with the liquid after insertion of the liquid receptacle. It is possible to exploit the fact that the change in the measured parameter increases with the increase in the axial speed which the output member and the piston plug for establishing the connection have relative to one another and that it can thus be more easily and reliably detected.

In some embodiments, the connecting mechanism preferably comprises a number of hooks, preferably a number of resilient hooks, which are configured in such a way that, during the axial advance of the output member to the piston plug or during the axial movement of the liquid receptacle in the direction of the output member, they yield substantially in the radial direction and subsequently spread out radially again. By engaging in at least one undercut which is rigidly coupled to, part of, integral with or carried by the piston plug, the hooks secure the connection against axial displacement of the output member relative to the piston plug. Since resilient hooks can be produced easily and inexpensively, it is possible, according to the invention, to obtain an inexpensive connecting mechanism.

In some embodiments, the undercut is preferably provided in the rear side of the piston plug facing toward the output member, preferably in a cavity of the piston plug, and it has a suitable profile adapted to the nature of the elements establishing the mechanical connection and to their geometry. To facilitate the release of the mechanical connection by relative twisting between piston plug and output member, the undercut of the connecting mechanism is preferably produced in the form of a screw-like thread, with a sense of rotation corresponding to the direction of rotation in which the mechanical connection is intended to be released by twisting. The screw-like thread preferably extends about several revolutions, and the thread height can be adapted to the form of the elements establishing the mechanical connection.

To ensure that the mechanical connection can be established easily and reliably, the connecting mechanism according to a first embodiment comprises a multiplicity of hooks which are distributed on the outer circumferential surface and protrude radially from the latter, the hooks also preferably being distributed along the longitudinal axis of the output member. Thus, it is possible to ensure that at least one of the multiplicity of hooks is present at a suitable axial position and angle for establishing the mechanical connection. The hooks can in this case be grouped into several rings which are distributed at different positions along the longitudinal axis of the output member and each comprise a plurality of hooks. In principle, the hooks can also be arranged randomly in terms of their axial position and angle. The number of the hooks is preferably sufficient that several of the hooks act as barbs and, in the connected state, the several barbs act counter to the advancing direction of the piston plug against one or several undercuts of the piston plug.

According to a preferred embodiment, the output member has an abutment on which the rear side of the piston plug directly bears when the mechanical connection is established. It is advantageous that, during the axial advance to the outlet of the liquid receptacle, the piston plug cannot deviate in the axial direction, with the result that the dose of liquid defined by the drive mechanics of the injection or infusion device can be administered exactly.

The aforementioned hooks or the element or several elements establishing the mechanical connection are preferably arranged, in one embodiment, in the axial direction, in front of the abutment of the output member.

In some embodiments, the hooks of the connecting mechanism are preferably pivotable or bendable substantially in the radial direction, and preferably without any great force being required for this. In this way, it is ensured that, during the axial advance of the output member to the piston plug or during the insertion movement of the receptacle, no substantial advancing force is exerted on the piston plug, with the result that no product is unintentionally dispensed.

According to a preferred embodiment, the hooks are designed as elastic elements and are made from a suitable material, for example plastic or metal, of suitable strength. Such elastic elements can be easily formed, in particular integrally formed, or fitted on the front end of the output member, and they dispense with the need for an additional and elaborate mechanism which would otherwise have to be provided in order to make the elastic elements pivotable or able to yield. In some embodiments, i is particularly preferable that they are flexurally elastic and act as bendable struts which are firmly clamped at one end.

According to a preferred embodiment, during the relative twisting of the output member with respect to the piston, the elastic elements of the connecting mechanism twist at least slightly, i.e., they yield elastically to a slight extent in the circumferential direction, so that only a relatively slight and thus negligible resistance force opposes the release of the connecting mechanism.

According to a further embodiment, the hooks of the connecting mechanism are designed as resilient claws mounted or carried at a front end of the output member. The claws are designed such that, in order to establish a mechanical connection between output member and piston plug, they engage in an opposite undercut. The claws are preferably substantially radially pivotable between a secured position, in which further pivoting of the claws is locked and which is used to secure the mechanical connection, and a released position in which the claws are pivoted radially back at least so far that the output member can be advanced to the piston plug or into the latter substantially without any resistance force.

In some embodiments, the resilient claws are preferably mounted on guiding and securing elements in such a way that, during the pivoting movement, the claws are guided straight and secure against twisting and are thus prevented from yielding in the circumferential direction. Thus, when they engage in the undercut, the claws do not deviate by executing a rotation movement, with the result that the mechanical connection between piston plug and output member can be made still more stable.

In some embodiments, the connecting mechanism preferably also comprises a restoring means which pre-tensions the resilient claws relative to one another. Upon engagement in the undercut, the resilient claws thus automatically straighten out again on account of the restoring force of the restoring means, in order to secure the mechanical connection between piston plug and output member.

According to a further embodiment, the connecting mechanism is designed such that the claws can be radially adjusted by being driven by a motor, for example with the aid of a spindle drive, in order to establish the mechanical connection between the output member and the piston plug. The torque at which the mechanical connection is made can thus be more precisely defined.

BRIEF DESCRIPTION OF THE DRAWINGS

FIG. 1, including FIGS. 1a-d, depicts an embodiment of the present invention, including a cross section through a connecting mechanism and an infusion pump, and a perspective view of the front end of an output member;

FIG. 2, including

FIG. 3, including

FIG. 4, including FIG. 5, including

DETAILED DESCRIPTION OF THE DRAWINGS

In the figures, identical reference numbers designate identical or substantially equivalent elements or groups of elements.

Figures 1, 1A:
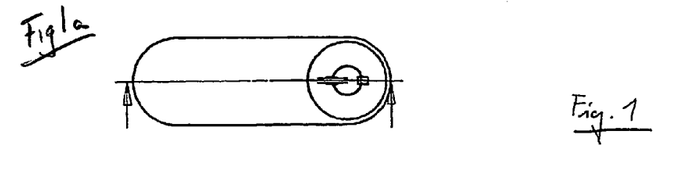
Figure 1B:
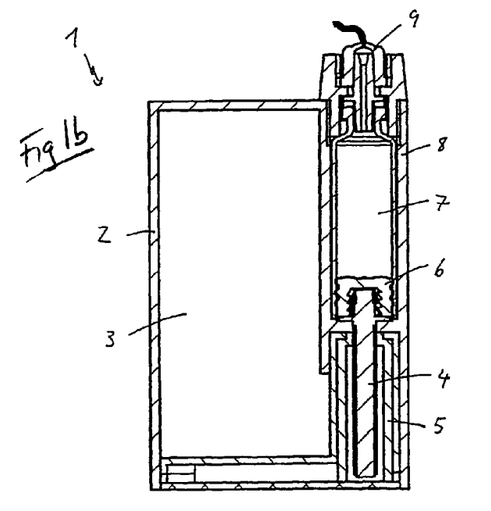
Figure 1C:
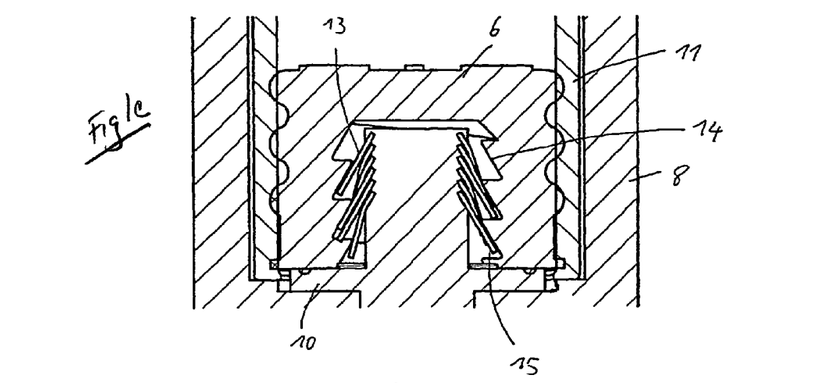
Figure 1D:
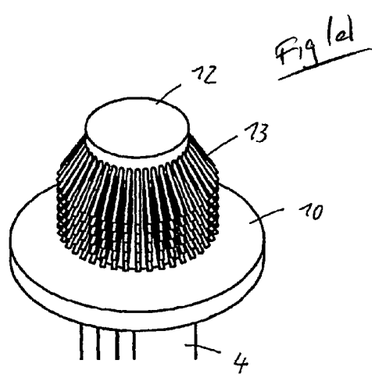

In FIG. 1, including FIGS. 1a-d, depicts an infusion pump according to one embodiment of the present invention is shown in cross section (FIG. 1b). FIG. 1c shows, in an enlarged cross section, the connecting mechanism according to this embodiment, and FIG. 1d shows, in a perspective view, the front end of the output member according to this embodiment. FIG. 1a depicts generally the location of the section line.

The infusion pump 1 is used, for example, for long-term administration of microdoses of a liquid stored in an ampule 7, said liquid containing a medical or therapeutic agent, preferably insulin, etc. The infusion pump 1 has a housing 2 which is substantially rectangular in cross section and whose interior 3 accommodates the mechanics and electronics (not shown) for controlling and/or operating the pump. Situated in the right-hand part of the infusion pump 1 is the substantially cylindrical ampule 7, which is received in a housing section 8 shaped corresponding to the ampule 7. A piston plug 6 (which also might be referred to as simply a piston or a plug), which is axially movable, is mounted in the ampule 7. The piston plug 6 is mechanically connected to the piston rod 4 which serves as the output member of the drive device (shown only schematically) for axial displacement of the piston rod 4 and of the piston plug 6. The piston rod 4 is guided rectilinearly in the lower part of the housing 2 and is in threaded engagement with a rotationally driven drive member 5. If the drive member 5 is driven in rotation, for example by an electric motor, the piston rod 4 undergoes an axial linear displacement. To dispense the product from the outlet 9 of the ampule 7, the piston rod 4 pushes the piston plug 6 toward the outlet 9. The ampule 7 is mounted in the housing section 8 so as to be exchangeable. To exchange the ampule 7, the connection between piston rod 4 and piston plug 6 has to be released. At the same time, for exact metering of the product, it is necessary that the connection between piston plug 6 and piston rod 4 be secured against axial displacement of the piston rod 4 relative to the piston plug 6.

According to the present invention, the connection between piston plug 6 and piston rod 4 can be released by relative twisting between piston plug 6 and piston rod 4, and the connection can be established by advancing the piston rod 4 onto the piston pug 6 or into it. Instead of this, or in combination with the advancing of the piston rod 4, the connection can be obtained by the oppositely directed movement of the ampule 7 during insertion.

As is shown in the right-hand part of FIG. 1, including FIGS. 1c and d, the front end of the piston rod 4 acting as output member comprises a number of resilient or at least resiliently mounted hooks 13 which, in the axial direction, are arranged in front of the circumferential projection 10 serving as abutment for the piston plug 6. In the illustrative embodiment, the hooks 13 are formed in the manner of flexurally elastic bristles of a brush and protrude obliquely downward from the piston rod 4 at an acute angle with respect to the axial direction in order, in this way, to form thin elastic struts clamped or attached securely at one end, their front end, to the rod 4. The resilient hooks 13 are grouped into several rings, in the example shown a total of five rings, the hooks 13 of a respective ring being arranged at approximately the same axial height, and the hooks 13 of the different rings being flush in the axial direction. Of course, the resilient hooks 13 can also be arranged at the front end of the piston rod 4 in some other way or may be unordered in the manner of a curling brush.

The resilient hooks 13 are made from a resiliently elastic material, for example from a plastic or a metal of low strength, so that, when they are subjected to a radially inwardly directed force, for example by contact with the undercut 15 (which also can be referred to as a relieved area or areas), the hooks 13 yield substantially in the radial direction by bending at their base and/or over their entire length and, after the force has ceased, they straighten again.

The upper part of FIG. 1, FIG. 1c, depicting the rear end of the ampule 7 in a greatly enlarged cross section, shows how the front end 12 of the piston rod 4 interacts with the piston plug 6. On its rear face, the piston plug 6 has a screw-like thread 14, and the thread 14 forms, in the axial direction, a plurality of undercuts which may be generally annular and arranged one behind the other and on which the resilient hooks 13 are supported in order to secure the axial position of the piston 6 relative to the piston rod 4 counter to the advancing direction. As can be seen from FIG. 1c, only some of the resilient hooks 13 are supported in the associated undercut 15 counter to the advancing direction, while others of the hooks 13 are not completely straightened again, i.e., are not yet spread radially outward to the unstressed position. If the front end of the piston rod 4 is let completely into the piston plug 6, the rear face of the piston plug 6 bears on the abutment 10.

To establish the connection between piston plug 6 and piston rod 4, the following procedure is followed: the ampule 7 is delivered in the rear end position, shown in FIGS. 1b and c, in which the rear face of the piston plug 6 bears, or almost bears, on the circumferential projection 10. After removal of a used ampule 7, the piston rod 4 is withdrawn axially into a rear end position. The new ampule 7 is then pushed into the housing section 8 until, finally, the front end of the piston rod 4 is pushed with the resilient hooks 13 into the piston plug 6. The resilient hooks 13 are bent radially inward by the undercuts 15, counter to their elastic restoring force. As the piston rod 4 is pushed farther into the open cavity on the rear face of the piston plug 6, some of the resilient hooks finally straighten again as they are pushed past the peaks of the undercuts 15 and they engage in an associated undercut 15 arranged approximately at the same height. As has been described, the connection shown can be obtained through axial advancing only of the piston rod 4, or only through the insertion of the ampule 7, or, although less preferable, through a combined movement. This is not intended to exclude the possibility that, during the advancing of the piston rod 4, a relative twisting may also be permitted between piston plug 6 and piston rod 4.

In the position shown in FIG. 1c, the piston plug 6 and the piston rod 4 cannot be pushed any farther toward one another, since the piston plug 6 is bearing on the abutment 10. Moreover, the piston plug 6 cannot be advanced axially relative to the piston rod 4, because some of the resilient hooks 13 are supported on the piston plug 6 counter to the advancing direction. Thus, the piston plug 6 is connected substantially rigidly to the piston rod 4.

To release the connection shown, the piston plug 6 may be twisted relative to the piston rod 4, specifically counter to the course of the screw thread 14, so that the resilient hooks 13 are unscrewed from the thread. For the release, the hooks 13 form the opposing thread for the thread 14 of the piston plug 6, which forms the undercuts 15.

In principle, the resilient hooks 13 do not need to be distributed about the entire circumference of the front end of the piston rod 4. Instead, the resilient hooks 13 can also be concentrated in particular angle regions, for example at two diametrically opposite locations. In an alternative embodiment of this kind, a relative twisting through 90 degrees would suffice to release the connection if, at the 90 degree angle position, an axially extending groove or the like is provided along which the resilient hooks 13 can be withdrawn from engagement with the piston plug 6.

Figure 2A:
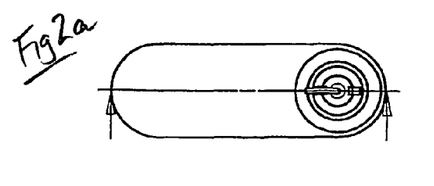
FIGS. 2a-e, depicts another embodiment of the present invention, including a cross section through a connecting mechanism and an infusion pump, and a perspective view of the front end of an output member.
Figure 2B:
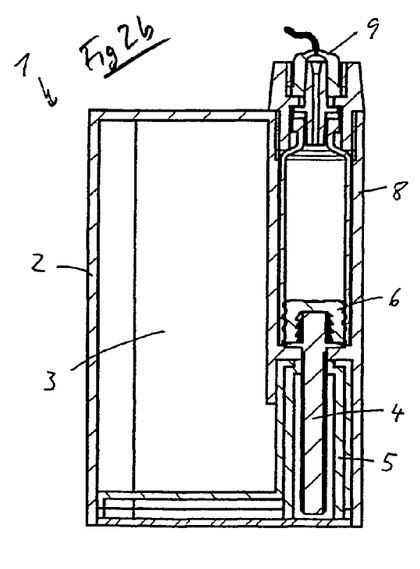
Figure 2C:
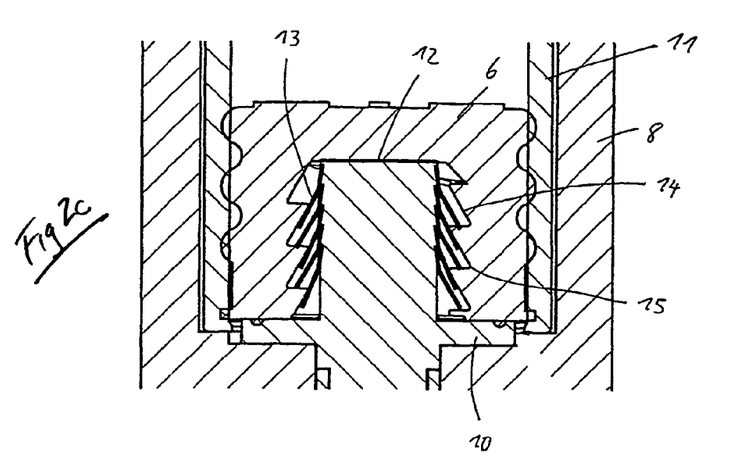
Figure 2D:
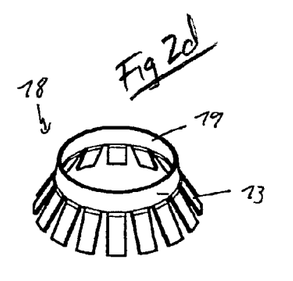
Figure 2E:
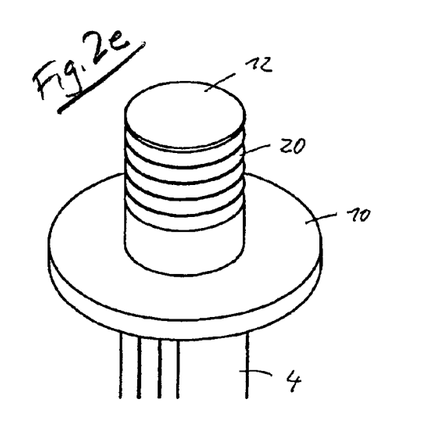

In FIG. 2, including FIGS. 2a-e, an infusion pump according to a second embodiment of the present invention is shown in cross section (FIG. 2b), and the front end of the piston rod 4 is shown in a perspective view (FIG. 2e). FIG. 2a depicts generally the location of the section line.

In principle, the second embodiment is different only in that several hook rings 18 (FIG. 2d) are fitted onto the front end of the piston rod 4. The hook rings 18 each comprise a circular ring 19 from which the flap-like hooks 13 protrude radially outward. The hook rings 18 are pushed onto the front end of the piston rod 4, where they each snap into a circumferential projection 20. According to the second embodiment, the hooks 13 preferably yield elastically only in the area of the base of the hook, that is to say in the connecting area between hook 13 and circular ring 19. However, this does not exclude that the hooks 13 can also be made of an elastic material, as in the first embodiment. The hook ring 18 is preferably produced by deep-drawing of a metal.

The connection between piston plug 6 and piston rod 4 is established by axially advancing the front end of the piston rod 4 into the piston plug 6 or by moving the ampule 7 axially directly at the time of insertion. To do so, no relative twisting need take place, although the latter is in principle possible. As in the first embodiment, the connection is released by relative twisting of the piston plug 6 in relation to the piston rod 4.

As can be seen from FIGS. 1 and 2, the connecting mechanism according to the some embodiments comprises a multiplicity of resilient hooks 13 which are formed at the front end of the piston rod 4. These are generally easy and inexpensive to produce. According to the present invention, however, it is also possible to use a smaller number of resilient hooks.

Figure 3A:
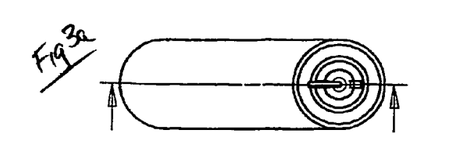
FIGS. 3a-d, depicts another embodiment of the present invention, including a cross section through a connecting mechanism and an infusion pump, and a perspective view of the front end of an output member.
Figure 3B:
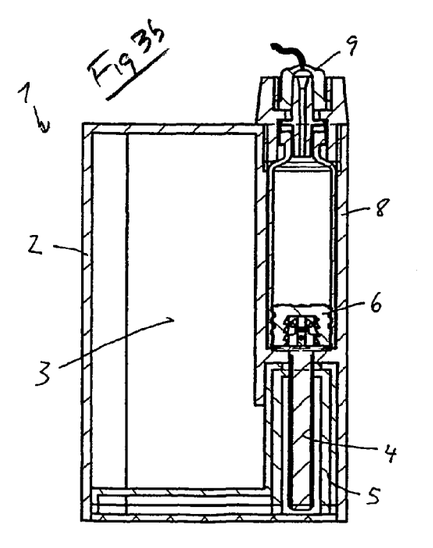
Figure 3C:
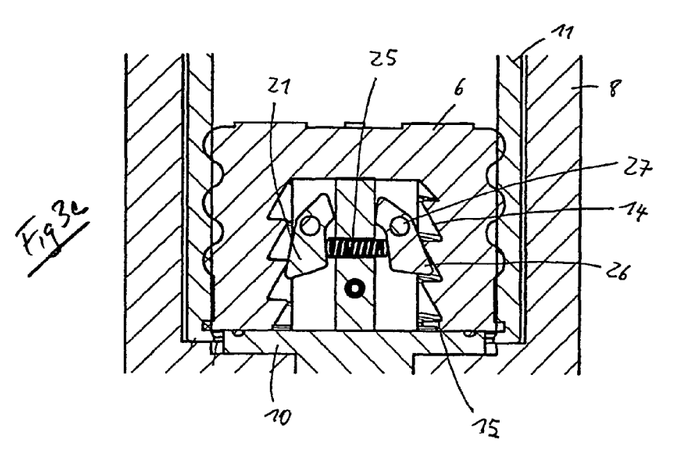
Figure 3D:
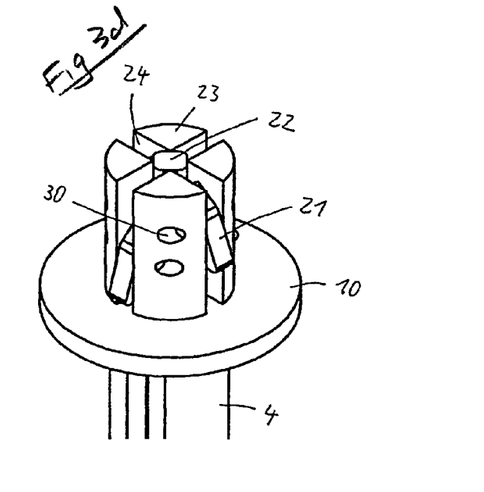

In FIG. 3, including FIGS. 3a-d, an infusion pump according to a third embodiment of the present invention is shown in cross section (FIG. 3b), and the front end of a piston rod according to this embodiment is shown in a perspective view (FIG. 3d). FIG. 3a depicts generally the location of the section line.

As shown in FIG. 3, including FIGS. 3c and d, four claws 21 are arranged at the front end of the piston rod 4. For this purpose, a central support 22 protrudes from the front end of the piston rod 4 together with a securing and guiding device 23 which is arranged around the support 22 and has a corresponding number of securing and guiding elements, four in the present illustrative embodiment. The claws 21 are each mounted so as to be pivotable, transverse to the axial direction, by way of pins 27 on the securing and guiding device 23. The openings 30 shown in the figure are provided for assembling the claws 21. The securing and guiding device 23 forms four gaps 24 which point in a star shape toward one another and in which the claws 21 are guided rectilinearly, so that the claws 21 are pivoted substantially only in axial planes about the pivot axes formed by the pins 27, and without being able to be twisted, such that the claws 21 do not yield in the circumferential direction when the connection is secured.

According to this embodiment, the four claws 21 are arranged in pairs at the same height, and the two pairs are axially offset with respect to one another. Like the hooks 13 discussed above, the claws 21 engage to different depths in the screw-shaped thread 14. This is illustrated in FIG. 3c, where the right-hand claw 21 engages deeper in the undercut or relieved area 15 than does the left-hand claw 21.

As can be seen FIG. 3c, two of the claws 21 are in each case pretensioned or urged radially outward with the aid of a compression spring 25 which serves as a restoring means and which can be formed with material elasticity as an elastomer ring or also with shape elasticity. The compression spring 25 is held on the support 22. Thus, in the rest state without stressing, the claws 21 protrude to the maximum extent radially from the front end of the piston rod 4. As the front end of the piston rod 4 and of the piston plug 6 are pushed over one another, the claws 21 which slide over the peaks of the thread 14 are pivoted radially inward. Upon further pushing-in, the restoring force of the compression spring 25 means that at least one of the claws 21 straightens out again into an opposite undercut 15, in order to lock the connecting mechanism.

In this embodiment, as in other embodiments, the thread 14 does not have to be formed about a full circumference.

Instead, it is sufficient if the thread 14 is formed only at locations where it lies opposite the claws 21 and if it is otherwise replaced by axially extending grooves or the like. Such grooves can be offset by an angle of 45 degrees relative to the claws 21 in the connecting position, so that the connection can be released again by simple twisting of the piston plug 6 and piston rod 4 through 45 degrees. However, in some preferred embodiments, the thread 14 extends continuously. It is also particularly advantageous that the piston plug 6 with thread 14 can be a conventional piston plug, in particular with a conventional thread 14, i.e., in some embodiments the invention requires no adaptation or modification as regards the piston plug.

According to another embodiment, which is shown in FIGS. 4 and 5, the pivotable claws 21 are forcibly pivoted, without the action of the undercuts 15, in order to establish the mechanical connection between piston plug 6 and output member 4.

Figures 4A, 4B, 4C, 4D:
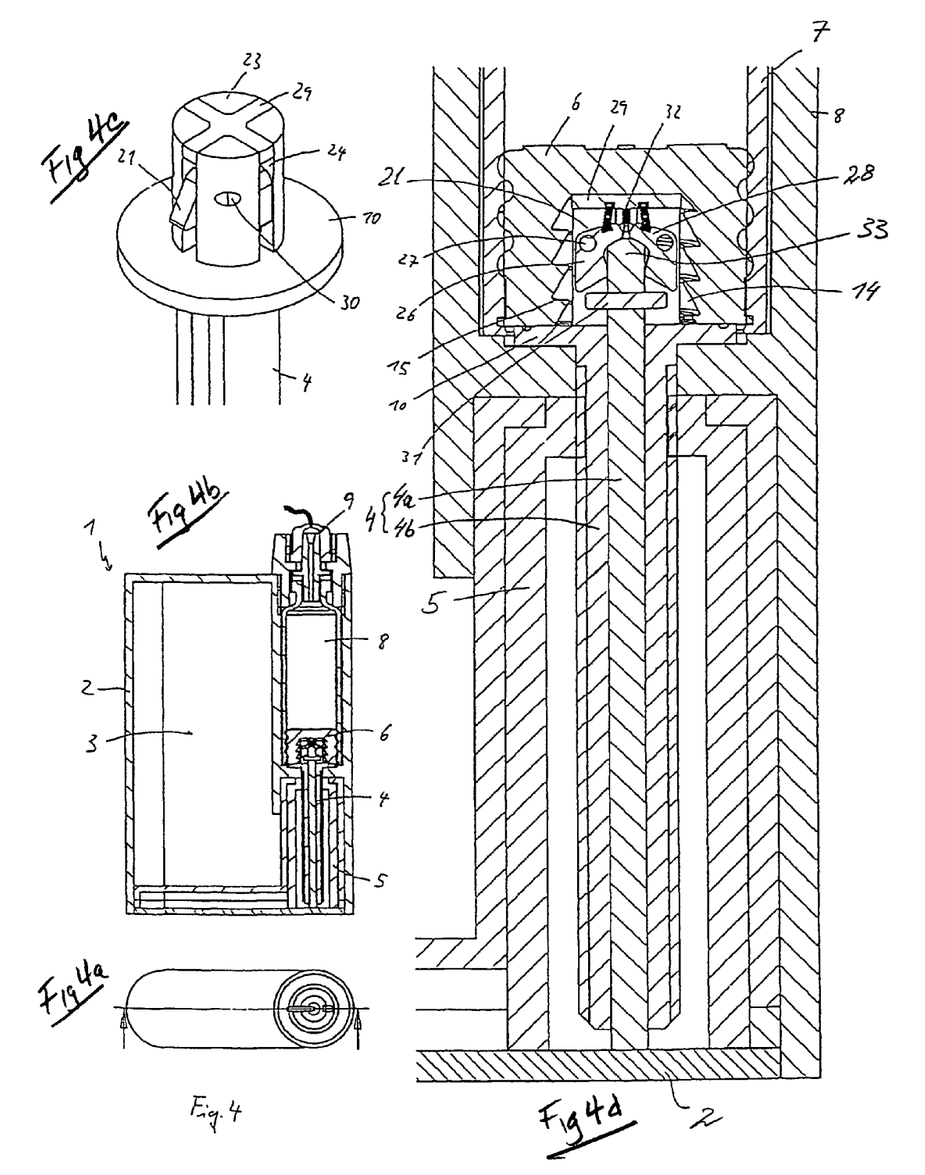
FIGS. 4a-d, depicts another embodiment of the present invention, including cross-sectional views of an infusion pump and a perspective view of the front end of an output member, shortly before the connection between the piston plug and the output member is established.

In this embodiment, as shown in FIGS. 4c and d and 5b and c, the piston rod 4 is in two parts and comprises a centrally arranged slide rod 4a, and a threaded sleeve 4b which surrounds the slide rod 4a and guides it in an axially linear manner. The threaded sleeve 4b has, along almost its entire axial length, an external thread which is interrupted over its axial length by a linear guide. The threaded sleeve 4b has its external thread in threaded engagement with an internal thread of the drive member 5. The drive member 5 is driven in rotation by a motor or other suitable means (not shown). The threaded sleeve 4b is guided axially from the housing 2 via its linear guide. A driving rotation movement of the drive member 5 therefore brings about the advance of the threaded sleeve 4b. As has already been mentioned, the slide rod 4a is received in the threaded sleeve 4b so that it is able to slide axially. A movement relative to the threaded sleeve 4b counter to the advancing direction is limited by an abutment shoulder 31 which is formed at the front end of the slide rod 4a and with which the slide rod 4a is supported on the front end of the threaded sleeve 4b.

In the position shown in FIG. 4, which the piston rod 4 assumes when a full ampule 7 is inserted, the slide rod 4a is also axially supported with its rear end on the housing 8. The slide rod 4a protrudes, with a headpiece 33 and with the abutment shoulder 31, axially above the abutment 10 of the threaded sleeve 4b and into the securing and guiding device 23 which is formed by the threaded sleeve 4b and in which several claws 21 are pivotably mounted. The guiding and securing device 23 and the claws 21 are formed generally like those of the embodiment of FIG. 3. The pins 27, in the present embodiment, too, again form the pivot axis for each of the claws 21. Viewed from the direction of the pins 27, each of the claws 21 forms an outer arm 26 and an inner arm 28. The claws 21 are each approximately L-shaped, the respective pivot axis being arranged in the area of the intersection of the two arms 26 and 28 of the L shape. Arranged between the cover 29, which is comparable to the cover of the illustrative embodiment of FIG. 3, and the respective inner arm 26 of each claw 21, there is a compression spring 32, i.e., one compression spring 32 per claw 21. The elastic spring forces of the compression springs 32 have the effect that the claws 21 spread radially outward about the pivot axes of the pins 27. This means, conversely, that, in order to insert the slide rod 4a into the cavity of the piston plug 6, the compression springs 32 are forcibly compressed and, in this way, the outer arms 26 are pivoted radially inward.

FIG. 4 shows the device in the state in which the arms 26 of the claws 21 are pivoted radially inward counter to the force of the respective compression spring 32. For this positioning of the claws 21, the slide rod 4a adopts its frontmost axial position relative to the threaded sleeve 4b, in which position the abutment shoulder 31 is axially spaced apart from the front end of the threaded sleeve 4b. The headpiece 33 presses like a ram against the inner arms 28 of the claws 21 in the advancing direction, so that the claws 21 are pivoted radially inward with their outer arms 26. The threaded sleeve 4b bears axially with its abutment 10 on the housing 8 counter to the advancing direction. In this state of the piston rod 4, the ampule 7 is pushed into the housing 8 counter to the advancing direction until the piston plug 6 sitting at the rear end of the ampule 7 is pushed onto the guiding and securing device 23. The pushing-on is not obstructed by the inwardly pivoted claws 26. After completion of this first phase of the procedure for establishing the connection, the device is in the state shown in FIG. 4, in which the piston plug 6, counter to the advancing direction, is in abutment contact with the abutment 10 of the threaded sleeve 4b and/or with the guiding and securing element 23, and in which the slide rod 4a adopts its frontmost axial position relative to the threaded sleeve 4b, in which position its abutment shoulder 31 has an axial clearance with respect to the front end of the abutment 10.

In order to establish the connection between the piston rod 4 and the piston plug 6, starting from the state shown in FIG. 4, the drive member 5 is driven in rotation so that the threaded sleeve 4b, by virtue of its linear guide, moves in translation in the advancing direction. In this forward movement, its abutment 10 lifts from the opposing abutment surface of the housing section 8, and the piston plug 6 sitting on the abutment 10 is moved together with the threaded sleeve 4b in the advancing direction. The tensioned compression springs 32 press the slide rod 4a via the claws 21 counter to the advancing direction. Since the slide rod 4a is blocked against an axial movement counter to the advancing direction, namely, in the illustrative embodiment, by being supported at its rear end on the housing 8, the compression springs 32 press with their elastic restoring forces on the inner arms 28 of the claws 21, such that the outer arms 26 pivot radially outward about the pins 27. The pivoting is ended when the claws 21 come into abutment with the rear surfaces of the undercuts 15 or when the abutment 10 comes into abutment contact with the abutment shoulder 31.

Figure 5A:
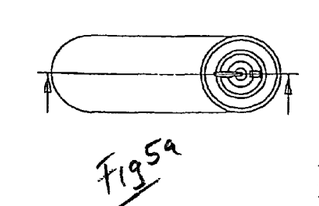
FIGS. 5a-c, depicts the embodiment of FIG. 4, including two cross-sectional views of an infusion pump after the connection between the piston plug and the output member has been established.
Figure 5B:
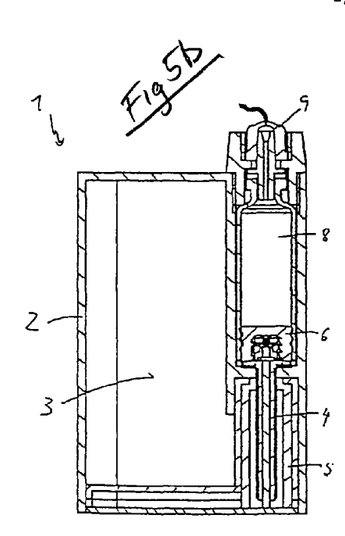
Figure 5C:
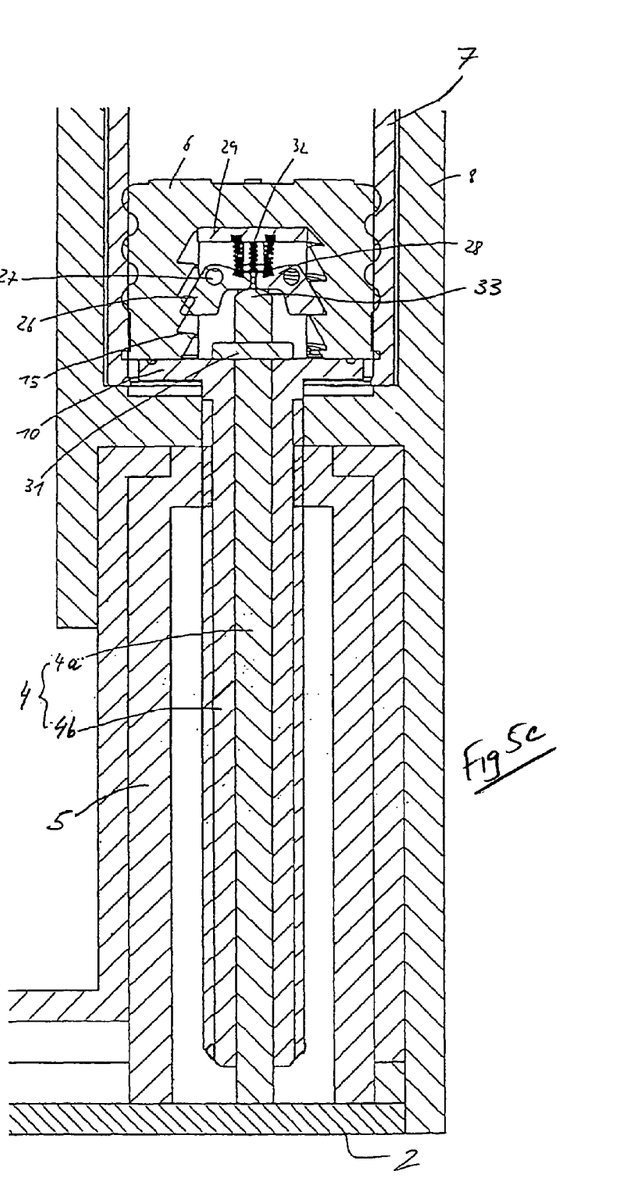

FIG. 5, including FIGS. 5a-c, shows the device in the state in which the connection between the piston rod 4 and the piston plug 6 is established. At least one of the total of four claws 21 is in abutment against a surface of the undercut 15 facing in the advancing direction, such that the piston rod 4 and the piston plug 6 are secured axially on one another. The pivot axes of all the claws 21, in the illustrative embodiment of four claws 21, are arranged at axially the same height. As in the other illustrative embodiments, the undercuts 15 may preferably be formed by a thread continuously extending in several revolutions.

To be able to move the slide rod 4a in the advancing direction in other axial positions of the piston rod 4 relative to the threaded sleeve 4b, in some embodiments, it is preferred if an adjustment means acts between the slide rod 4a and the threaded sleeve 4b. The adjustment means can be formed, for example, by magnetically coupling the slide rod 4a and the threaded sleeve 4b by electromagnets. An adjustment means with a purely mechanical action is also conceivable.

Although the connecting mechanism has been described above with reference to a motor-driven infusion pump, the invention is not limited to this. Instead, the connecting mechanism can also be used on or in other delivery devices, such as injection devices in which the ampule containing the product is intended to be exchanged.

When using such injection or infusion devices to treat diabetes by administration of insulin, it has proven particularly advantageous to use gauge 30 or gauge 31 hollow needles, which are fitted on the outlet of the liquid receptacle.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for the administration of a liquid product, comprising a receptacle for storing the product, a piston plug axially moveable in an advancing direction toward an outlet of the receptacle by an output member, and a connecting mechanism comprising a plurality of hook elements comprised of flexurally elastic bristles spaced about a non-threaded portion of an outer circumferential surface of the output member, wherein the flexurally elastic bristles are arranged in at least one ring and protrude obliquely away from the advancing direction of the output member, said connecting mechanism for releasably connecting the piston plug to the output member by way of the flexurally elastic bristles to secure a connection between piston plug and output member against axial displacement of the output member relative to the piston plug wherein the connection between the piston plug and output member is releasable by relative twisting between the piston plug and the output member.

2. The device as claimed in claim 1, the piston plug comprising a cavity defined by a plurality of threads, and the connecting mechanism hook elements comprising the flexurally elastic bristles moveable in a substantially radial direction during axial displacement of the output member.

3. The device as claimed in claim 2, in which the plurality of threads defining the cavity comprise screw-like threads.

4. The device as claimed in claim 1, in which the output member comprises an abutment for abutting a surface of the piston plug, and the hook elements are arranged in front of the abutment in the axial direction.

5. The device as claimed in claim 1, in which the hook elements of the connecting mechanism are configured to pivot or bend counter to elastic restoring forces, such that connection between the piston plug and the output member is established by axial, linear displacement of the output member relative to the piston plug.

6. The device as claimed in claim 1, in which the hook elements are configured to yield in the circumferential direction during the relative twisting of the output member with respect to the piston plug, such that the connection between the piston plug and output member is releasable by relative twisting between the piston plug and the output member.

7. The device as claimed in claim 1, in which the hook elements are radially displaceable by a motor for establishing the connection between piston plug and output member.

8. The device as claimed in claim 1, in which a 30 gauge or 31 gauge hollow needle for dispensing the product is secured on the outlet.

9. A device for administering a liquid product, comprising a receptacle for the product, a piston plug axially moveable by an output member in an advancing direction toward an outlet of the receptacle to cause product to be dispensed from the receptacle, and a connecting mechanism comprising a plurality of hook elements comprised of flexurally elastic bristles disposed on a non-threaded surface and arranged in at least one ring configuration arranged on one of the piston plug and an outer circumferential portion of the output member and a cavity defined by threaded walls disposed on the other of the piston plug and the outer circumferential portion of the output member, the connecting mechanism for releasably connecting the piston plug to the output member, wherein a connection between the piston plug and the output member is established by axial, linear displacement of the output member and the piston plug relative to one another, wherein when the piston plug and the output member are connected, said connecting mechanism prevents axial displacement of the output member and of the piston plug relative to one another, and wherein the connection is releasable by relatively twisting the piston plug and the output member.

10. The device as claimed in claim 9, wherein one of the piston plug and output member comprises at least one relieved area associated with the cavity, and the other component of the connecting mechanism comprising the plurality of hook elements moveable in a substantially radial direction during the axial displacement, so that, by engaging the at least one of the plurality of hook elements in the at least one relieved area, the axial displacement of the output member relative to the piston plug is prevented.

11. A device for the administration of a liquid product, comprising a receptacle for storing the product, a piston plug comprising a cavity defined by screw-like threads, the piston plug axially moveable in an advancing direction toward an outlet of the receptacle by an output member to cause product to be dispensed from the receptacle, and a connecting mechanism comprising a plurality of hook elements formed of flexurally elastic bristles spaced about a non-threaded portion of an outer circumferential surface of the output member for releasably connecting the piston plug to the output member to secure a connection between piston plug and output member against axial displacement of the output member relative to the piston plug, the connection being established by engagement of one or more of the plurality of flexurally elastic bristles of the connecting mechanism with the screw-like threads of the piston plug, and the connection being releasable by relative twisting between the piston plug and the output member.

12. The device as claimed in claim 11, in which the output member comprises an abutment for abutting a surface of the piston plug, and the hook elements are arranged in front of the abutment in the axial direction.

13. The device as claimed in claim 11, wherein the flexurally elastic bristles protrude radially from a front end of the output member.

14. The device as claimed in claim 11, in which a 30 gauge or 31 gauge hollow needle for dispensing the product is secured on the outlet.

15. The device as claimed in claim 1, wherein the hook elements are clamped around an outer circumferential surface of the output member in a plurality of rings, the plurality of rings arranged in the axial direction of the output member, and the plurality of hook elements configured to engage with the screw-like threads of the piston plug.

16. The device as claimed in claim 15, wherein hook elements provided in each respective ring are arranged at approximately the same axial height.

17. The device as claimed in claim 16, wherein the hook elements of the different rings are flush in the axial direction.

18. The device as claimed in claim 15, wherein the flexurally elastic bristles are formed as struts.

19. The device as claimed in claim 9, wherein the hook elements are clamped around an outer circumferential surface of the output member in a plurality of rings, the plurality of rings arranged in the axial direction of the output member, and the plurality of hook elements configured to engage with the screw-like threads of the piston plug.

20. The device as claimed in claim 19, wherein hook elements provided in each respective ring are arranged at approximately the same axial height.

21. The device as claimed in claim 20, wherein the hook elements of the different rings are flush in the axial direction.

22. The device as claimed in claim 19, wherein the flexurally elastic bristles are formed as struts.

23. The device as claimed in claim 13, wherein the hook elements are clamped around an outer circumferential surface of the output member in a plurality of rings, the plurality of rings arranged in the axial direction of the output member, and the plurality of hook elements configured to engage with the screw-like threads of the piston plug.

24. The device as claimed in claim 23, wherein hook elements provided in each respective ring are arranged at approximately the same axial height.

25. The device as claimed in claim 24, wherein the hook elements of the different rings are flush in the axial direction.

26. The device as claimed in claim 23, wherein the flexurally elastic bristles are formed as struts.

* * * * *